United States Patent
Liao et al.

(10) Patent No.: US 9,776,956 B2
(45) Date of Patent: Oct. 3, 2017

(54) METHOD FOR PREPARING N,N'-BIS(2-CYANOETHYL)-1,2-ETHYLENEDIAMINE BY USING CATION EXCHANGE RESIN AS CATALYST

(71) Applicant: NAN YA PLASTICS CORPORATION, Taipei (TW)

(72) Inventors: Te-Chao Liao, Taipei (TW); Jung-Jen Chuang, Taipei (TW); Zhi-Ming Huang, Taipei (TW); Shun-Chi Chen, Taipei (TW); Tzu-Chiang Lin, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 15/355,108

(22) Filed: Nov. 18, 2016

(65) Prior Publication Data

US 2017/0152216 A1 Jun. 1, 2017

(30) Foreign Application Priority Data

Nov. 26, 2015 (TW) .............................. 104139365 A

(51) Int. Cl.
*C07C 253/18* (2006.01)

(52) U.S. Cl.
CPC .................................. *C07C 253/18* (2013.01)

(58) Field of Classification Search
None
See application file for complete search history.

(56) References Cited

U.S. PATENT DOCUMENTS

2008/0194857 A1* 8/2008 Hayes .................. C07C 209/48
558/452

* cited by examiner

*Primary Examiner* — Samantha Shterengarts
(74) *Attorney, Agent, or Firm* — Bacon & Thomas, PLLC

(57) ABSTRACT

A method for preparing N,N'-bis(2-cyanoethyl)-1,2-ethylenediamine involves using strongly acidic cation exchange resin as a catalyst for synthesis, and is advantageous for not only eliminating the need of distillation for purification and thereby reducing reaction time, but also improving the yield of N,N'-bis(2-cyanoethyl)-1,2-ethylenediamine to 97.70-98.08%; and the method benefits simplified process and reduced costs and helps to save water significantly, thereby minimizing environmental pollution.

14 Claims, No Drawings

METHOD FOR PREPARING N,N'-BIS(2-CYANOETHYL)-1,2-ETHYLENEDIAMINE BY USING CATION EXCHANGE RESIN AS CATALYST

BACKGROUND OF THE INVENTION

1. Field of the Invention

The present invention relates to N,N'-bis(2-cyanoethyl)-1,2-ethylenediamine (hereinafter shortened as BCNEDA), and more particularly to a method for preparing BCNEDA with improved yield.

2. Description of Related Art

Conventionally, synthesis of BCNEDA uses acetic acid, water, monol-based solvent (e.g., ethanol, isopropanol or methanol) or other promoters as a catalyst for promoting reaction. However, acetic acid can corrode the equipment and other solvents are not helpful to enhance the yield of BCNEDA so there is a need of distillation for product purification.

For example, DE 2446489A1 has in 1976 disclosed a process wherein acrylonitrile and ethylenediamine at a molar ratio of 2:1 are used. Acrylonitrile containing therein acetic acid as a catalyst is added into ethylenediamine (EDA) within 2 hours. According to this disclosed process, the obtained product after distillation can give BCNEDA at a yield of 98.1%. Nevertheless, acetic acid used in the process can corrode the equipment and this prevented the process from commercial applications.

As another example, US 2008/0194857A1 discloses a method wherein water is used as a solvent and then acrylonitrile and ethylenediamine at a molar ratio of 2:1 react in the presence of 2-30 wt % of water based on the total reactants to synthesize N,N'-bis(2-cyanoethyl)-1,2-ethylenediamine When the amount of water is 20 wt %, the yield of BCNEDA reaches 93.78%.

Additionally, it is known in the art to use a monol-based solvent (e.g., ethanol, isopropanol or methanol) as a catalyst and to have acrylonitrile and ethylenediamine at a molar ratio of about 2:1 react in the presence of 60-120 wt % of a monol-based solvent based on total reactants, thereby synthesizing BCNEDA. The ethanol solvent provides the most preferred result for it gives a yield of BCNEDA as high as 97.60%.

SUMMARY OF THE PRESENT INVENTION

To break the stereotype that BCNEDA is conventionally made in the presence of acetic acid, water or monol-based solvent as the solvent, the present invention discloses a method for preparing BCNEDA with high selectivity, wherein strongly acidic cation exchange resin is used instead of the conventional solvents such as acetic acid, water and monol-based solvent. Without using any solvents, the need of distillation for purification is eliminated and the yield of BCNEDA is improved to 97.7% or more, even to 97.70-98.08%. The method benefits form simplified process and reduced costs and helps to save water significantly, thereby minimizing environmental pollution.

The disclosed method for preparing BCNEDA comprises the following synthesis steps:
1. in a reactor (such as a three-neck round-bottom flask), adding ethylenediamine and 20-100 wt % of strongly acidic cation exchange resin based on the weight of ethylenediamine; and
2. adding acrylonitrile dropwise so that a molar ratio between ethylenediamine and acrylonitrile is 1:1.9-2.1 while holding the temperature below 70° C.; after dropwise addition, at a temperature 20-70° C., preferably at room temperature, i.e. 25° C., allowing the reaction to continue for 5-30 more minutes; upon completion of reaction, using gas chromatography (GC) to analyze the reaction product and determine the yield of BCNEDA is 97.7% or more.

The strongly acidic cation exchange resin is bead-form sulfonic-acid-based and carboxylic-acid-based cation exchange resin, and is preferably Amberlyst-15 or Amberlyst-36 cation exchange resin. The strongly acidic cation exchange resin has an average diameter ($D_{50}$) of 0.1-1.0 mm, and is characterized in having a total exchange capacity (or total capacity) greater than 1.7 eq/L.

The strongly acidic cation exchange resin is regenerable and can be filtered and recycled. The method for preparing BCNEDA according to the present invention has the following advantages:
1. improving the yield of BCNEDA to 96.0% or more;
2. simplifying the manufacturing because the need of distillation for purification is eliminated, and reducing manufacturing costs because the cation exchange resin can be recycled and reused; and
3. effectively eliminating the problems about equipment corrosion caused by solvents and about waste water as well as waste liquids.

DETAILED DESCRIPTION OF THE INVENTION

The method for preparing BCNEDA according to the present invention takes ethylenediamine and acrylonitrile at a certain ration as reactants to react in the presence of strongly acidic cation exchange resin for synthesis. The final reactants after reaction need not distillation for purification and give an improved yield of BCNEDA of 97.7% or more, even as high as 97.70-98.08%.

The disclosed method for preparing BCNEDA comprising the following steps:
a) using cation exchange resin as a catalyst for synthesis;
b) adding ethylenediamine and the cation exchange resin of step a) to a reactor (such as a three-neck round-bottom flask), wherein the cation exchange resin is used in an amount of 50-100 wt % based on the weight of the ethylenediamine reactant;
c) at 25-70° C., adding acrylonitrile dropwise that a molar ratio between ethylenediamine and acrylonitrile is 1:1.9-2.1, while the temperature is held below 70° C. to prevent acrylonitrile form self-polymerization at a temperature higher than 70° C.; and
d) after dropwise addition, allowing the reaction to continue for 5-30 more minutes at 20-70° C., preferably at room temperature, before completion of the reaction, and a reaction product is obtained; subsequently, gas chromatography is used to verify the reaction product which is a mixture of containing N,N'-bis(2-cyanoethyl)-1,2-ethylenediamine In the foregoing method for preparing BCNEDA, acrylonitrile may be added in any of the alternative ways described below to achieve the yield of BCNEDA of 97.70% or more:
1. adding ethylenediamine and acrylonitrile simultaneously and continuously into the reactor;
2. adding acrylonitrile continuously into the reactor; or
3. mixing acrylonitrile and cation exchange resin and then adding the mixture continuously into the reaction.

The critical technique of the disclosed method for preparing BCNEDA relies on using bead-form cation exchange resin as the catalyst for synthesis, so as to improve the yield of BCNEDA to 97.70-98.08% or more. The process is simple and safe and eliminates the need of distillation for purification. In addition, the process causes no corrosion to the equipment and effectively solves the problems about waste water and waste liquids.

The cation exchange resin is strongly acidic cation exchange resin, for converting (or decomposing) cations of normal salts in water (shortened as decomposing normal salts). The cation exchange resin selected from sulfonic-acid-based or carboxylic-acid-based cation exchange resin, and preferably is Amberlyst-15 or Amberlyst-36 cation exchange resin.

The bead-form cation exchange resin has an average diameter ($D_{50}$) of 0.1-1.0 mm and is characterized in having a total exchange capacity (or total capacity) greater than 1.7 eq/L. Therein, the term "total exchange capacity" refers to the equivalent number of $H^+$ provided by cation exchange resin that is sufficiently acidified and decomposes normal salt.

The cation exchange resin is regenerable and can be filtered and recycled.

While the following examples are herein discussed for further explaining the present invention, the scope of the present invention is not limited thereto.

EXAMPLE 1

In a 250 mL three-neck flask, 12.002 g (0.200 mol) of ethylenediamine (hereinafter shortened as EDA) and 6.001 g of strongly acidic cation exchange resin (Amberlyst 36wet) were introduced. At room temperature, 21.827 g (0.411 mol) of acrylonitrile (hereinafter shortened as ACN) was added dropwise with the temperature held below 70° C. in the whole process.

After addition of ACN, reaction continuously took place for 30 minutes at 25° C. (without heating) until completion to obtain a final reaction product. Gas chromatography (hereinafter shortened as GC) was used to analyze the reaction product in terms of composition, and the results are shown in Table 1. The yield of BCNEDA is 97.70%.

EXAMPLE 2

The process was similar to that of Example 1, but the strongly acidic cation exchange resin used was 9.602 g instead of 6.001 g. After the reaction, the reaction product was analyzed in terms of composition, and the results are shown in Table 1. The yield of BCNEDA is 97.82%.

EXAMPLE 3

The process was similar to that of Example 1, but the cation exchange resin used was 12.002 g instead of 6.001 g. After the reaction, the reaction product was analyzed in terms of composition, and the results are shown in Table 1. The yield of BCNEDA is 97.75%.

EXAMPLE 4

The process was similar to that of Example 3, but the reaction duration was 5 minutes instead of 30 minutes before completion. After the reaction, the reaction product was analyzed in terms of composition, and the results are shown in Table 1. The yield of BCNEDA is 98.08%.

COMPARATIVE EXAMPLE 1

Without using cation exchange resin, 12.002 g (0.200 mol) of ethylenediamine (EDA) was introduced into a 250 mL three-neck flask. At room temperature, 21.198 g (0.3995 mol) of acrylonitrile (ACN) was added dropwise with the temperature held below 70° C. in the whole process.

After addition of ACN, reaction continuously took place for 30 minutes at 25° C. (without heating) until completion to obtain a final reaction product. Gas chromatography (hereinafter shortened as GC) was used to analyze the reaction product in terms of composition, and the results are shown in Table 1. The yield of BCNEDA is 81.28%.

COMPARATIVE EXAMPLE 2

In a 250 mL three-neck flask, 12.002 g (0.200 mol) of ethylenediamine (EDA) and 0.120 g of cation exchange resin (Amberlyst 36wet) were introduced. At room temperature, 21.30 g (0.401 mol) of acrylonitrile (ACN) was added dropwise with the temperature held below 70° C. in the whole process.

After addition of ACN, reaction continuously took place for 30 minutes at 25° C. (without heating) until completion to obtain a final reaction product. Gas chromatography (hereinafter shortened as GC) was used to analyze the reaction product in terms of composition, and the results are shown in Table 1. The yield of BCNEDA is 80.69%.

COMPARATIVE EXAMPLE 3

The process was similar to that of Comparative Example 2, but the cation exchange resin used was 0.600 g instead of 0.120 g. After the reaction, the reaction product was analyzed in terms of composition, and the results are shown in Table 1. The yield of BCNEDA is 80.81%.

COMPARATIVE EXAMPLE 4

The process was similar to that of Example 1, but the cation exchange resin used was 2.400 g instead of 6.001 g. After the reaction, the reaction product was analyzed in terms of composition, and the results are shown in Table 1. The yield of BCNEDA is 92.44%.

TABLE 1

| Components | Examples | | | | Comparative Examples | | | |
|---|---|---|---|---|---|---|---|---|
| (wt %) | 1 | 2 | 3 | 4 | 1 | 2 | 3 | 4 |
| Ethylenediamine[1] (g) | 12.002 | 12.002 | 12.002 | 12.002 | 12.002 | 12.002 | 12.002 | 12.002 |

TABLE 1-continued

| Components (wt %) | Examples | | | | Comparative Examples | | | |
|---|---|---|---|---|---|---|---|---|
| | 1 | 2 | 3 | 4 | 1 | 2 | 3 | 4 |
| Acrylonitrile[2] (g) | 21.827 | 21.827 | 21.827 | 21.827 | 21.198 | 21.300 | 21.300 | 21.827 |
| Molar ratio EDA/ACN | 1/2.06 | 1/2.06 | 1/2.06 | 1/2.06 | 1/2.00 | 1/2.01 | 1/2.01 | 1/2.06 |
| Cation Exchange Resin[3] (g) | 6.001 | 9.602 | 12.002 | 12.002 | — | 0.120 | 0.600 | 2.400 |
| Weight Ration of Cation Exchange Resin to Ethylenediamine | 50% | 80% | 100% | 100% | 0% | 1% | 5% | 20% |
| Reaction Duration (minutes) | 30 | 30 | 30 | 5 | 30 | 30 | 30 | 30 |
| BCNEDA[4] yield (%) | 97.70 | 97.82 | 97.75 | 98.08 | 81.28 | 80.69 | 80.81 | 92.44 |

Note:
[1]Ethylenediamine, produced by Tedia Company, Inc.;
[2]Acrylonitrile, produced by Hayashi Pure Chemical Ind., Ltd.;
[3]Cation exchange resin, produced by Rohm and Haas Company;
[4]Yield (%) = Conversion (%) × Selectivity (%)

CONCLUSION

1. As demonstrated in Examples 1-4 and Comparative Example 1, in the process of preparing BCNEDA, by using a specific amount of strongly acidic cation exchange resin as the catalyst for synthesis, the yield of BCNEDA is improved.

2. As learned from Comparative Examples 3-4 and Examples 1-4, in the process of preparing BCNEDA, where the amount of strongly acidic cation exchange resin is below 20 wt % based on the weight of the ethylenediamine reactant, the yield of BCNEDA is limited to 92.44%.

3. As demonstrated in Examples 1-4 and Comparative Example 4, in the process of preparing BCNEDA, by using ethylenediamine and acrylonitrile at a specific ration to react in the presence of 50-100 wt % of strongly acidic cation exchange resin based on the weight of the ethylenediamine reactant for synthesis reaction, adding acrylonitrile dropwise, and continuing the reaction for 5-30 minutes at 25° C. (without heating), the yield of BCNEDA can be significantly improved to 97.70-98.08%.

4. As learned by comparing Examples 1-3 and Example 4, in the disclosed process for preparing BCNEDA, by adding acrylonitrile dropwise and then allowing the reaction to continue for 5 minutes at 25° C. (without heating), the yield of BCNEDA can be as high as 98.08%.

What is claimed is:

1. A method for preparing N,N'-bis(2-cyanoethyl)-1,2-ethylenediamine, comprising steps of: taking ethylenediamine and acrylonitrile at a molar ratio therebetween of 1:1.9-2.1 as reactants to perform synthesis reaction in the presence of strongly acidic cation exchange resin for 5-30 minutes at a temperature of 20-70° C. thereby obtaining N,N'-bis(2-cyanoethyl)-1,2-ethylenediamine with a yield of 97.7% or more; wherein the strongly acidic cation exchange resin is sulfonic-acid-based or carboxylic-acid-based cation exchange resin and is used in an amount of 50-100 wt % based on a weight of the ethylenediamine reactant.

2. The method of claim 1, wherein the strongly acidic cation exchange resin is bead-form sulfonic-acid-based or carboxylic-acid-based cation exchange resin, with an average diameter ($D_{50}$) of 0.1-1.0 mm and has a total exchange capacity greater than 1.7 eq/L.

3. The method of claim 1, wherein the strongly acidic cation exchange resin is Amberlyst-15 or Amberlyst-36 cation exchange resin.

4. The method of claim 2, wherein the strongly acidic cation exchange resin is Amberlyst-15 or Amberlyst-36 cation exchange resin.

5. The method of claim 1, wherein the molar ratio between ethylenediamine and acrylonitrile is 1:2.06.

6. The method of claim 2, wherein the molar ratio between ethylenediamine and acrylonitrile is 1:2.06.

7. The method of claim 1, wherein the synthesis reaction performs continuously for 5-30 minutes at room temperature of 25° C.

8. The method of claim 2, wherein the synthesis reaction performs continuously for 5-30 minutes at room temperature of 25° C.

9. The method of claim 1, wherein the acrylonitrile is added dropwise into a reactor.

10. The method of claim 2, wherein the acrylonitrile is added dropwise into a reactor.

11. The method of claim 1, wherein the acrylonitrile is continuously added but not added dropwise into a reactor.

12. The method of claim 2, wherein the acrylonitrile is continuously added but not added dropwise into a reactor.

13. The method of claim 11, wherein the acrylonitrile is added into the reactor simultaneously with ethylenediamine in a continuous manner.

14. The method of claim 11, wherein the acrylonitrile is added into the reactor simultaneously with the cation exchange resin in a continuous manner.

* * * * *